United States Patent [19]
Fessi et al.

[11] Patent Number: 5,118,528
[45] Date of Patent: * Jun. 2, 1992

[54] PROCESS FOR THE PREPARATION OF DISPERSIBLE COLLOIDAL SYSTEMS OF A SUBSTANCE IN THE FORM OF NANOPARTICLES

[75] Inventors: Hatem Curt Fessi, Paris; Jean-Philippe Devissaguet, Neuilly S/Seine; Francis Puisieux, Maisons Alfort, all of France; Curt Thies, St. Louis, Mo.

[73] Assignee: Centre National de la Recherche Scientifique, Paris, France

[*] Notice: The portion of the term of this patent subsequent to Sep. 17, 2008 has been disclaimed.

[21] Appl. No.: 593,522

[22] Filed: Oct. 4, 1990

Related U.S. Application Data

[63] Continuation of Ser. No. 140,245, Dec. 31, 1987, abandoned.

[30] Foreign Application Priority Data

Dec. 31, 1986 [FR] France .................. 86 18446

[51] Int. Cl.⁵ .................. A61K 9/51; B01J 13/06; B01J 13.12
[52] U.S. Cl. .................. 427/213.36; 264/4.1; 264/4.6; 424/469; 424/485; 424/486; 424/487; 428/402.2; 428/402.21; 514/965
[58] Field of Search .................. 264/4.6; 427/213.36; 424/469, 485, 486, 487; 514/965

[56] References Cited

U.S. PATENT DOCUMENTS

| | | | |
|---|---|---|---|
| 3,691,090 | 9/1972 | Kitajima et al. | 264/4.6 |
| 4,492,720 | 1/1985 | Mosier | 427/213.3 |
| 4,585,651 | 4/1986 | Beck et al. | 424/89 X |

FOREIGN PATENT DOCUMENTS

| | | |
|---|---|---|
| 495261 | 8/1978 | Australia . |
| 738604 | 8/1943 | Fed. Rep. of Germany . |
| WO86/03676 | 7/1986 | PCT Int'l Appl. . |
| 201942 | 12/1938 | Switzerland . |

*Primary Examiner*—Richard D. Lovering
*Attorney, Agent, or Firm*—Young & Thompson

[57] ABSTRACT

The process according to the invention comprises: (1) the preparation of a liquid phase consisting essentially of a solution of the substance in a solvent or in a mixture of solvents to which may be added one or more surfactants, (2) the preparation of a second liquid phase consisting essentially of a non-solvent or a mixture of non-solvents for the substance and to which may be added one or more surfactants, the non-solvent or the mixture of non-solvents for the substance being miscible in all proportions with the solvent or the mixture of solvents for the substance, (3) the addition of one of the liquid phases prepared in (1) or (2) to the other with moderate stirring so as to produce a colloidal suspension of nanoparticles of the substance, and (4) is desired, the removal of all or part of the solvent or the mixture of solvents for the substance and of the non-solvent or the mixture of non-solvents for the substance so as to produce a colloidal suspension of nanoparticles of the desired concentration or to produce a powder of nanoparticles.

16 Claims, No Drawings

PROCESS FOR THE PREPARATION OF DISPERSIBLE COLLOIDAL SYSTEMS OF A SUBSTANCE IN THE FORM OF NANOPARTICLES

This application is a continuation of application Ser. No. 07/140,245, filed Dec. 31, 1987, now abandoned.

The subject of the present invention is a novel procedure for the preparation of dispersible colloidal systems of a substance in the form of spherical particles of the matrix type and of a size less than 500 nm (nanoparticles).

Sub-microscopic particles of a diameter less than 500 nm are already known, in particular from the patents BE-A-808 034, BE-A-839 748, BE-A-869 107 and FR-A-2 504 408. According to BE-A-808 034 and -839 748, the sub-microscopic particles are formed by micellar polymerization of a monomer such as a derivative of acrylic acid. Similarly, BE-A-869 107 and FR-A-2 504 408 describe the preparation of biodegradable nanoparticles obtained by the polymerization of an alkyl cyanoacrylate and containing a biologically active substance. The methods resort to polymerization in solution and are thus limited to using a limited number of polymers which can be prepared, in particular, by vinyl addition and are not suitable for naturally occurring or semi-synthetic polymers. Furthermore, it is difficult to control the molecular weight of the polymer constituting the nanoparticles and it is necessary, particularly when their biological use is under consideration, to remove the residual monomers and oligomers and, where necessary, the excess reagents involved in the polymerization reaction (initiator and catalyst), as well as the surfactants if they are used at high concentration or are not biocompatible. In actual fact, the purification often proves to be onerous (ultracentrifugation, dialysis) since the filtration of the nanoparticles is not always possible on account of their size.

Methods employing emulsification-evaporation have also been described which make use of preformed polymers and according to which an organic solution of polymer, immiscible with water, is emulsified in a continuous aqueous phase, then the solvent is evaporated in order to give rise to a suspension of polymer insoluble in water. However, while the major relevance of this method lies in its applicability to numerous polymers of synthetic or semi-synthetic origin and thus in the possibility of producing nanoparticles from well-defined polymers, the disadvantage associated with it resides in the difficulty of preparing ultra-fine and homogeneous emulsions for the production of nanoparticles smaller than 500 nm and homogeneous in size. Furthermore, the necessity of often having to use surfactants in high proportions (20%) and which must be removed, and the use of sophisticated equipment with high energy requirements (sonicators, homogenizers, ...) constitute serious handicaps to their industrial application.

The production of nanoparticles has also been suggested in the case of proteins, in particular by heat denaturation of a water-in-oil emulsion of a solution of a protein such as albumin (Kramer, P. A.: J. Pharm. Sci., 63, 1646 (1974), or by the desolvation of a protein solution such as gelatin by means of a mineral salt or ethanol (Marty et al., in Austr. J. Pharm. Sci., 6, 65 (1978) or in Pharm.Acta. Helv. 53, No. 1 (1978)), followed, in both cases, by hardening by means of an aldehyde. The main disadvantage of the method of Kramer is the need to emulsify beforehand the aqueous solution of the macromolecular starting material in a continuous oily phase. Since this emulsion must be very fine, the use of surfactants and the necessary equipment (sonicator, etc) is essential for the production of nanoparticles of appropriate size. As for the method of Marty, it requires the use of considerable amounts of mineral salts which must be removed, as well as the excess of aldehyde and the sulfite or metabisulfite used to neutralize the latter.

All of the methods described above are only applicable to certain classes of molecules and necessarily involve operations which are expensive (ultracentrifugation, sonication, etc) or hard to control (polymerization) without ensuring that the size of the particles is acceptable homogeneous or even that the particles are sufficiently small (less than 500 nm) such as would assure their long-term stability in the form of a colloidal suspension.

The invention proposes a new process for the preparation of nanoparticles which is free from the above-mentioned disadvantages and which can be used both for naturally occurring and synthetic polymeric substances and for various organic substances (medicines, lipids, etc) or minerals (salts, pigments, etc) as well as for mixtures of them.

The subject of the present invention is a process for the preparation of dispersible colloidal systems of a substance in the form of spherical particles of the matrix type and of a size less than 500 nm (nanoparticles), comprising:
(1) the preparation of a liquid phase consisting essentially of a solution of the substance in a solvent or in a mixture of solvents to which one or more surfactants may be added,
(2) the preparation of a second liquid phase consisting essentially of a non-solvent or a mixture of non-solvents of the substance to which one or more surfactants may be added, the non-solvent or the mixture of non-solvents for the substance being miscible in all proportions with the solvent or mixture of solvents for the substance,
(3) the addition of one of the liquid phases prepared in (1) or (2) to the other with moderate agitation so as to produce a colloidal suspension of nanoparticles of the substance, and
(4) if desired, the removal of all or part of the solvent or the mixture of solvents for the substance and of the non-solvent or the mixture of non-solvents for the substance so as to give rise to a colloidal suspension of nanoparticles of the desired concentration or to lead to a powder of nanoparticles.

In step (3), the nanoparticles are formed practically instantaneously. The solution becomes milky-white and shows the Tyndall effect characteristic of colloidal suspensions. At this stage, it is preferable to add the liquid phase prepared in step (1) to the liquid phase prepared in step (2), particularly if the latter is aqueous, but the reverse order is possible as the examples show.

The "substance" used according to the process of the invention may be practically any substance sufficiently soluble in a given solvent.

The "substance" may be, in particular, a film-forming material such as a polymer, either a synthetic polymer, for example poly (d,1) lactic acid (PLA), etc, a semi-synthetic polymer such as for example cellulose butyrate acetate, ethylcellulose, the phthalate of hydroxymethyl-propylcellulose (HPMCP), etc, or a naturally occurring polymer, for example gelatin, gum arabic, etc. Numerous other polymers can be used, for example: the aceto-phthalate of polyvinyl, the aceto-phthalate of cellulose: maleic acid derivatives (for example "Gantrez"); the copolymers of acrylic acid and acrylates and acrylic acid polymers (for example Eudragit ®); d or 1 or (d,1) polylactic acid; the copolymers of lactic acid and glycolic acid, polypeptides, glycol derivatives (derivatives of propiolactone, butyrolactone, pivalolactone, ε-caprolactone, etc); the polymers obtained from cyclic esters of hydroxybutyric acid, hydroxyisobutyric acid, hydroxymethylvaleric acid, phenyllactic acid, hydroxyethylbutyric acid; poly beta benzyl malate; the copolymers of malic acid and benzyl maleate; a polyvinylpyrrolidone-vinyl acetate cross-linked copolymer, alkyl polycyanoacrylates; poly (ethylene-vinyl acetate); water-soluble polymers (gelatin, gum arabic, methylcellulose, etc); oligomers (styrene allyl alcohol), etc.

The "substance" may be a fatty substance, for example a mono-, di-, or tri-glyceride of a fatty acid; a hydrogenated oil such as, for example, hydrogenated castor oil, an oil solid at room temperature, such as for example copra oil; a wax such as for example beeswax, an ester formed between a fatty acid and polyethylene glycol (PEG), as for example the distearate of PEG 6000, etc.

The "substance" may also be a biologically active substance, in particular a medicamentous active ingredient or a precursor of a medicamentous active ingredient or even a contrasting agent or a biological reagent. In such a case, it may be of interest to prepare nanoparticles comprising both a biologically active substance and a film-forming material such as a polymer as "substance" as will be seen later.

The "substance" may also be a pigment, an ink, a lubricant, an agent for treating surfaces, etc.

It is obvious that the process according to the invention can be applied equally to one substance or to several.

In this respect, according to a variant of the process, a second substance may be bound by absorption to the surface of nanoparticles already formed in step (3) by simple addition to the colloidal suspension of the polymer, if necessary after concentration. This second substance may be in particular a biologically active substance.

The "solvent" or the mixture of solvents used is a liquid capable of dissolving the substance (for example, the polymer and/or the biologically active substance). Moreover, the solvent must be miscible with the non-solvent for the substance used in the preparation. Thus, in most cases, the solvent will be an organic solvent such that the liquid phase (1) will constitute the organic phase whereas the liquid phase (2) will constitute the aqueous phase, but it is possible to use either two organic phases or two aqueous phases provided the conditions regarding solubility, insolubility and miscibility are met. On the other hand, the solvent must be sufficiently volatile for it to be removed if necessary. For example, in the case in which the substance is a polymer (to which a biologically active substance has or has not been added), the solvent may be chosen from among a lower alcohol (methanol, ethanol, isopropanol, etc), a lower ketone (acetone, methyl-ethyl-ketone, etc), a light hydrocarbon or a mixture of light hydrocarbons (hexane, petroleum ether, etc), a chlorinated light hydrocarbon (chloroform, methylene chloride, trichloroethylene, etc) or other common light solvents such as acetonitrile, dioxane etc.

The "non-solvent" or the mixture of non-solvents for the substance is a liquid which does not dissolve the substance while being miscible with the solvent used. Thus, for example, when the substance is a polymer such as PLA, the solvent may be acetone and the non-solvent may be ethanol or distilled water; if the substance is for example an acrylic polymer such as Eudragit L100 ®, the solvent may be an alkaline aqueous phase and the non-solvent may be an acidic aqueous phase. It may be advantageous to add a low proportion (lower than 20% by volume, for example about 10% by volume) of non-solvent to the solvent in liquid phase (1) as this will make it possible to produce smaller nanoparticles, in particular particles less than 100 nm.

In order to produce a more stable suspension it is desirable to add one or more surfactants (or emulsifying agents). The surfactants may be anionic (for example sodium laurylsulfate), cationic (for example, quaternary ammonium) or non-ionic (for example, monoesters of sorbitan which may or may not contain a polyoxyethylene residue, ethers formed between fatty alcohols and polyoxyethylene glycols, polyoxyetheylene-polypropylene glycol, etc).

However, the nanoparticles may be produced according to the invention without surfactants and, moreover, the latter are not necessary if all of the solvents and non-solvents are eliminated in step (4), for example by lyophilization. In this way, lyophilized nanoparticles may be produced which can be stored for long periods.

The proportion of surfactants in the colloidal suspension prepared in step (3) to which they have been added may vary in particular from 0.1% to 10% by weight, and preferably between 0.2 and 2% by weight.

In the case in which the substance is a polymer, the concentration of the polymer in the solvent or the mixture of solvents may vary between 0.1 and 10%, and preferably between 0.2 and 2% by weight.

The ratio of the volumes of the solvents and non-solvents must be such as to allow the precipitation of the polymer. As this ratio increases, the size of the nanoparticles diminishes.

The need for moderate agitation of the preparation in step (3) is dependent on the amount of substances utilized. It is not necessary for small quantities.

The effect of temperature and pH on the process according to the invention are so limited that it is usually not necessary to work under special conditions. However, when the two phases (1) and (2) used are aqueous, their respective pHs must be different in order for them to comply with the conditions of being a solvent and a non-solvent.

Moreover, the presence of an electrolyte (for example sodium chloride) does not appear to affect the production of nanoparticles. Thus, after the formation of the nanoparticles in Example 1, a concentration of 25 mg/ml sodium chloride does not lead to coalescence or precipitation of the nanoparticles formed.

The particles produced according to the invention can be autoclaved if the physical properties of the substance permit this.

The process for the preparation of nanoparticles according to the invention offers the following advantages compared with known processes:

the production of nanoparticles smaller than 500 nm and in particular of about 200 nm by means of a simple method not requiring a supply of energy;

in the case in which the substance comprises a polymer, the nanoparticles are no longer produced by polymerization of a monomer but by "nanoprecipitation" of a well-defined polymer;

the utilization of naturally occurring polymers as well as synthetic polymers which are known to be innocuous and which have been used for medical purposes for a very long time;

the utilization of polymers which are of the type which are biocompatible;

the possibility of using polymers which can dissolve in the organism once a particular pH value is attained, thus ensuring that polymer particles do not accumulate in the organism;

the possibility of using polymers which by their nature are bioresorbable, the products of their degradation being completely innocuous;

the production of spherical particles exhibiting only a slight variation in size.

The following examples illustrate the invention. The nanoparticles obtained are visible in the transmission electron microscope (×25.000–150,000) and, after negative staining with phosphotungstic acid, appear as approximately round, non-contrasted particles.

EXAMPLE 1

Preparation of nanoparticles of polymers

On the one hand, 125 mg of poly (d,1) lactic acid (P.L.A.) are dissolved in 25 ml of acetone and, on the other hand, 125 mg of the mixed polymer formed between ethylene oxide and propylene glycol (Pluronic F68 ® or Poloxamer 188), a non-ionic surfactant, are dissolved in 50 ml of purified water.

The acetone phase is added to the aqueous phase with magnetic stirring (100 r.p.m.). The mixture immediately becomes opalescent as a result of the formation of nanoparticles of the polymer (P.L.A.). The mean diameter of the nanoparticles measured in a diffractometer equipped with a laser beam (Nanosizer ® supplied by the Coultronics Company) immediately after preparation is about 200 nm with a dispersion index of 0.5.

The acetone is removed under reduced pressure (water pump vacuum) and the suspension is concentrated to the desired volume, for example 10 ml, under the same conditions.

The concentrated suspension of nanoparticles is filtered through a glass frit (pores 9–15 μm) or through a membrane filter (pores 5 μm) and the diameter of the nanoparticles, measured again in the filtrate, remains unchanged as does the dispersion index. Examination in the transmission electron microscope reveals the nanoparticles of poly (d,1) lactic acid to be regular spheres.

After prolonged standing (18 months) the appearance of the suspension of nanoparticles remains unchanged and, in particular, neither irreversible sedimentation nor variation in the size of the nanoparticles is observed.

EXAMPLE 2

Variant of Example 1

The process described in Example 1 is employed but the aqueous phase is added to the acetone phase. The nanoparticles produced have the same properties as those in Example 1.

EXAMPLE 3

Variant of Example 1

The process described in Example 1 is employed but the acetone phase is added to the aqueous phase without stirring. The nanoparticles produced have a mean diameter of 205 nm with a mean dispersion index of 1.

EXAMPLE 4

Variant of Example 1

The process described in Example 1 is employed but without the addition of a surfactant to the aqueous phase. The nanoparticles produced have a mean diameter of 207 nm with a mean dispersion index of 1.3.

EXAMPLE 5

Preparation of nanoparticles containing indomethacin (lipophilic active ingredient)

a) The process described in Example 1 is employed but 5 mg of indomethacin are added to the acetone phase. The nanoparticles produced have a mean diameter of 180 nm with a mean dispersion index of 1.5. After ultracentrifugation and titration of the indomethacin in the phase used as dispersion medium, the amount of active ingredient incorporated into the nanoparticles amounts to 80% of the amount initially present.

b) Pharmacological assay:

When administered by the oral route to the fasted rat (5 mg/kg of indomethacin) the suspension of nanoparticles leads to a more rapid and more complete digestive absorption of the indomethacin than that observed after administration of the same dose of indomethacin in solution. After repeated administration to the fasted rat (5 mg/kg of indomethacin on 3 successive days) the suspension of nanoparticles results in improved digestive tolerance, as evidenced by the number of ulcerations and hemorrhages, compared with that observed after administration of the same dose of indomethacin in solution.

When administered by the intravenous route to the rat (5 mg/kg of indomethacin) the suspension of nanoparticles gives rise to a chronological profile of plasma concentrations of indomethacin which demonstrates an increased extravascular distribution of the active ingredient compared with that found after injection of indomethacin in solution (increase of the volume of distribution of indomethacin by a factor of approximately 2), followed by slower elimination (increase of the biological half-life of indomethacin by a factor of approximately 2).

EXAMPLE 6

Preparation of nanoparticles containing doxorubicin (hydrophilic active ingredient)

a) The process described in Example 1 is employed but 12.5 mg of doxorubicin are added to the aqueous phase. The nanoparticles produced have a mean diameter of 288 nm with a mean dispersion index of 2. After ultracentrifugation and titration of the doxorubicin in the phase used as dispersion medium, the amount of active ingredient incorporated into the nanoparticles amounts to 50% of the quantity initially present.

b) Pharmacological assay:

When administered to the rat at a dose of 10 mg/kg for three days, the suspension of doxorubicin nanoparticles showed a marked improvement in cardiac toxicity of the active ingredient compared with its administration in solution, results comparable with those observed by COUVREUR et al. (J. Pharm. Sci., 71, p. 790, (1982) with nanoparticles prepared by polymerization of isobutyl cyanoacrylate.

EXAMPLE 7

Binding of an active ingredient (doxorubicin) to nanoparticles of polymer.

The process described in Example 1 is employed. Subsequently, 12.5 mg of doxorubicin are added to the suspension of nanoparticles of P.L.A. concentrated to a volume of 10 ml. After 72 h of contact the mean diameter of the nanoparticles is about 220 nm with a mean dispersion index of 2. After ultracentrifugation and titration of the doxorubicin in the phase used as dispersion medium, the amount of active ingredient bound to the nanoparticles amounts to 32% of the quantity initially present.

EXAMPLE 8

Addition of non-solvent to the solvent phase

The process described in Example 1 is employed but the polymer is dissolved in an acetone/water (90/10, v/v) mixture instead of pure acetone. The presence of a low proportion of non-solvent for the polymer in its solvent leads to nanoparticles, the mean diameter of which is about 90 nm with a mean dispersion index of 1.5.

EXAMPLE 9

Use of two aqueous phases a) On the one hand, 625 mg of an acrylic polymer (Eudragit L 100 ®) are dissolved in 125 ml of purified water to which 3.45 ml of 0.1N sodium hydroxide are added.

On the other hand, 625 mg of the mixed polymer formed from ethylene oxide and propylene glycol (Pluronic F68 ®) are dissolved in 250 ml of purified water to which 0.85 ml of glacial acetic acid is added.

The basic polymer aqueous phase is added to the acidic aqueous phase with magnetic stirring. The nanoparticles of Eudragit L100 ® form immediately, turning the medium opalescent. After concentration of the suspension under reduced pressure, the mean diameter of the nanoparticles is about 130 nm with a mean dispersion index of 2.3.

b) Preparation of tablets. The suspension of nanoparticles of Eudragit L100 ® obtained above was used to prepare a tablet coating formulation by atomization. The coated tablets showed that they were gastro-resistant for at least 2 h at acid pH (gastric medium of the U.S. Pharmacopoeia) but released their active ingredient at neutral pH (intestinal medium of the U.S. Pharmacopoeia).

EXAMPLE 10

Use of two polar organic phases

On the one hand, 125 mg of poly (d,l) lactic acid are dissolved in 25 ml of tetrahydrofuran.

On the other hand, 125 mg of the mixed polymer formed between ethylene oxide and propylene glycol (Pluronic F 68 ®) are dissolved in 50 ml of absolute ethanol.

The polymer phase is added to the ethanolic phase with magnetic stirring. The nanoparticles of poly (d,l) lactic acid form immediately, turning the medium opalescent. After concentration of the suspension to a volume of 4 ml under reduced pressure and at low temperature, followed by filtration through a glass frit (pores 9-15 μm), the mean diameter of the nanoparticles is about 201 nm with a mean dispersion index of 1.6.

EXAMPLE 11

Use of two apolar organic phases a) On the one hand, 125 mg of acrylic polymer (Eudragit L100 ®) are dissolved in 25 ml of chloroform.

On the other hand, 0.2 ml of sorbitan mono-oleate (SPAN 80 ®, non-ionic surfactant) are dissolved in 50 ml of heptane.

The chloroform phase is added to the heptane phase with magnetic stirring. The nanoparticles of Eudragit L100 ® form immediately, turning the medium opalescent.

After concentration of the suspension to a volume of 30 ml, the nanoparticles have a mean diameter of 350 nm with a mean dispersion index of 1.

b) Preparation of tablets.

When used under the same conditions as those in Example 9b, the suspension of nanoparticles of Eudragit L100 ® enabled gastro-resistant, coated tablets to be manufactured.

EXAMPLE 12

Preparation of nanoparticles of lipid

On the one hand, 125 mg of the stearate of glycerol are dissolved in an acetone/tetrahydrofuran (90/10, v/v) mixture.

On the other hand, 0.25 ml of the polyoxyethylene derivative of sorbitan mono-oleate (TWEEN 80 ®), non-ionic surfactant) are dissolved in 50 ml of purified water.

The lipid organic phase is added to the aqueous phase with magnetic stirring. The nanoparticles of the stearate of glycerol form immediately, turning the medium opalescent.

After concentration of the suspension to a volume of 10 ml, the nanoparticles have a mean diameter of 300 nm with a mean dispersion index of 3.

EXAMPLE 13

Variant of Example 12

On the one hand, 125 mg of the palmito-stearate of glycerol and 0.1 ml of sorbitan mono-oleate (SPAN 80 ®) are dissolved in 50 ml of absolute ethanol.

On the other hand, 0.1 ml of the polyoxyethylene derivative of sorbitan mono-oleate (TWEEN 80 ®) are dissolved in 50 ml of purified water.

The lipid alcoholic phase is added to the aqueous phase with magnetic stirring. The nanoparticle of the palmito-stearate of glycerol form immediately, turning the medium opalescent.

After concentration of the suspension to a volume of 10 ml, the nanoparticles have a mean diameter of 160 nm with a mean dispersion index of 2.

EXAMPLE 14

Preparation of nanoparticles of indomethacin a) The process described in Example 1 is employed but the polymer is replaced by 25 mg of indomethacin.

After concentration of the suspension by evaporation of the organic solvent, the nanoparticles of indomethacin of a mean diameter of 290 nm with a mean dispersion index of 2. Examination in the transmission electron microscope reveals that the nanoparticles of indomethacin are spherical and non-crystalline.

b) Pharmacological assay:

When administered by the oral route to the fasted rat (5 mg/kg), the suspension of nanoparticles of indomethacin leads to more rapid and more complete absorption than that observed after administration of equivalent doses of indomethacin in solution.

When administered by the intravenous route to the rat (5 mg/kg), the suspension of nanoparticles of indomethacin gives rise to a chronological profile of plasma concentrations of indomethacin which demonstrates an increased extravascular distribution of the active ingredient compared with that found after injection of equivalent doses of indomethacin in solution (increase of the volume of distribution), followed by slower elimination (increase of the biological half-life).

EXAMPLE 15

Lyophilization of nanoparticles of polymer

The process described in Example 1 is employed. After concentration of the suspension of nanoparticles of P.L.A. to a volume of 20 ml, 200 mg of trehalose are added and the suspension is lyophilized.

After dispersion of the lyophilisate in 10 ml of purified water, the nanoparticles have a mean diameter of 275 nm with a mean dispersion index of 1.5.

EXAMPLE 16

Stability of nanoparticles of polymer at varying ionic strengths

The process described in Example 1 is employed. After concentration of the suspension of nanoparticles of P.L.A. to a volume of 10 ml, increasing amounts of sodium chloride are progressively added to it. The suspension of nanoparticles is perfectly stable when the concentration of sodium chloride renders it isotonic with blood and remains so up to concentrations of sodium chloride more than three times higher than the isotonic concentration.

EXAMPLE 17

Preparation of nanoparticles in the presence of a salt

The process described in Example 1 is employed but 90 mg of sodium chloride is added to the aqueous phase. After concentration of the suspension of nanoparticles to a volume of 10 ml, corresponding to a sodium chloride concentration with the isotonicity of blood, the nanoparticles have a mean diameter of 250 nm with a mean dispersion index of 2.

The suspension remains stable with time and, after being stored for 12 months, shows neither irreversible sedimentation nor variation in the size of the nanoparticles.

It is possible that the nanoparticles produced according to the invention will find uses in many areas of technology.

As "vectors" of medicines in human and animal therapy, the nanoparticles offer the prospects of:
attaining new sites of action, in particular intracellular sites, and even intralysosomal sites;
using new routes of administration for known medicines by increasing the stability and/or the absorption of the medicines, or by making available insoluble medicines in forms which can be injected by the intravascular route;
modifying the tissue distribution of the medicines by better targetting towards favourable sites of action and/or by diverting them from sites at which they produce undesirable, or even toxic, effects (improvement of the therapeutic index).

In pharmacy, the colloidal dispersions in the form of nanoparticles make it possible to:
prepare injectable forms of insoluble medicines,
stablilize a medicamentous active ingredient, and
prepare coatings of galenical forms starting from aqueous dispersions of film-forming polymers.

In the field of agrochemistry, the nanoparticles can be used as vehicles for insecticides, pesticides, etc . . . Their size leads to the expectation of a more powerful action as a result of better penetration through the cuticle. The low viscosity of the dispersion enables atomization to be carried out very easily in the form of droplets of very small size which are more efficacious because they provide more intimate covering.

In the area of paints, varnishes and treatment of surfaces in general, the nanoparticles may function as vehicles of pigments, reagents, strippers, etc . . . in the form of aqueous dispersions of very low viscosity, easy to atomize or apply and which can, if necessary, be made viscous and even adhesive (resuspension of the nanoparticles in an appropriate vehicle). A small size of the nanoparticles leads to a very fine deposition and to a very high homogeneity, for example, of pigmentation.

The nanoparticles produced according to the invention can also be used in the fields of printing and reproduction graphics, the treatment of surfaces of textiles and fibres, photography, lubrication, etc . . .

What we claim is:

1. A process for the preparation of dispersible colloidal systems of a substance in the form of spherical particles of the matrix type and of a size less than 500 nm (nanoparticles), comprising:

combining (1) a first liquid phase consisting essentially of a solution of a film-forming material and a biologically active substance in a solvent or in a mixture of solvents to which may be added one or more surfactants, and (2) a greater volume of a second liquid phase consisting essentially of a non-solvent or a mixture of non-solvents for the film-forming material and biologically active substance and to which may be added one or more surfactants, the non-solvent or the mixture of non-solvents for the film-forming material and biologically active substance being miscible in all proportions with the solvent or mixture of solvents for the film-forming material and biologically active substance;

thereby substantially instantaneously to precipitate from said solvent and said non-solvent composite particles of said film-forming material and biologically active substance to produce a colloidal suspension of composite nanoparticles.

2. The process according to claim 1, further comprising removing at least a portion of the solvent or the mixture of solvents and of the non-solvent or mixture of non-solvents thereby to produce a colloidal suspension of nanoparticles of a desired concentration, or to produce a powder of nanoparticles.

3. The process according to claim 2, wherein said solvents and non-solvents are substantially completely removed by lyophilization.

4. The process according to claim 1, wherein said combining step comprises adding said first liquid phase to said second liquid phase.

5. The process according to claim 1, wherein a lesser amount of non-solvent is used to form said second phase than solvent used to prepare said first liquid phase.

6. The process according to claim 1, wherein said colloidal suspension comprises 0.1 to 10% by weight of at least one surfactant.

7. The process according to claim 6, wherein said at least one surfactant is present in said colloidal suspension in an amount of 0.2 to 2% by weight.

8. The process according to claim 1, wherein said film-forming material is a polymer.

9. The process according to claim 8, wherein said polymer is present in said first liquid phase in an amount of 0.1 to 10% by weight.

10. The process according to claim 9, wherein the concentration of the polymer is between 0.2 and 2% by weight.

11. The process according to claim 8, wherein a second substance is bound to the nanoparticles of said colloidal suspension.

12. The process according to claim 11, wherein said second substance is a biologically active substance.

13. The process according to claim 1, wherein said biologically active substance is a fatty substance.

14. The process according to claim 1, wherein the nanoparticles have a diameter of about 200 nm.

15. A process for the preparation of dispersible colloidal systems of a substance in the form of spherical particles of the matrix type and of a size less than 500 nm (nanoparticles), comprising:

combining (1) a first liquid phase consisting essentially of a solution of a polymer in a solvent or in a mixture of solvents to which may be added one or more surfactants, and (2) a greater volume of a second liquid phase consisting essentially of a non-solvent or a mixture of non-solvents for the polymer and to which may be added one or more surfactants, the non-solvent or the mixture of non-solvents for the polymer being miscible in all proportions with the solvent or mixture of solvents for the polymer;

thereby substantially instantaneously to precipitate from said solvent and said non-solvent particles of said polymer to produce a colloidal suspension of nanoparticles.

16. The process according to claim 15, wherein the polymer is polylactic acid.

* * * * *